United States Patent [19]

Lewis

[11] 4,091,921
[45] May 30, 1978

[54] STERILIZABLE PACKAGE AND METHOD

[75] Inventor: Robert P. Lewis, Oceanport, N.J.

[73] Assignee: Faser Industries, Saddle Brook, N.J.

[21] Appl. No.: 780,141

[22] Filed: Mar. 22, 1977

Related U.S. Application Data

[63] Continuation-in-part of Ser. No. 606,510, Aug. 21, 1975.

[51] Int. Cl.² .............................................. B65D 83/10
[52] U.S. Cl. .................................. 206/363; 206/459; 206/534
[58] Field of Search ............... 206/438, 439, 459, 498, 206/533, 534, 538, 539, 534.2, 63.3, 363; 116/114 AM, 114 AJ, 114 F, 114 V; 73/356; 229/53

[56] References Cited

U.S. PATENT DOCUMENTS

| | | | |
|---|---|---|---|
| 3,093,242 | 6/1963 | Huyck | 206/459 |
| 3,123,210 | 3/1964 | Hermanson | 206/439 |
| 3,419,137 | 12/1968 | Walck | 206/484 |
| 3,429,433 | 2/1969 | Holt | 206/459 |
| 3,460,742 | 8/1969 | Langdon | 206/439 |
| 3,527,400 | 9/1970 | Shepherd | 206/459 |
| 3,616,898 | 11/1971 | Massie | 206/216 |
| 3,650,391 | 3/1972 | Chung | 206/526 |
| 3,991,881 | 11/1976 | Augert | 206/439 |

*Primary Examiner*—Herbert F. Ross
*Attorney, Agent, or Firm*—Burgess, Dinklage & Sprung

[57] ABSTRACT

A sterilizable package having a plastic member marginally heat sealed to a paper member to which is applied indicia that changes color upon sterilization (gas and/or steam) on the inside of the package. The indicia is located in or near the marginal heat seal and is segregated from the package interior to prevent the package contents from covering or being contaminated by coming in contact with the indicia by heat sealing the plastic member to the paper member in the area of the indicia. The indicia can be located within the area covered by the marginal heat seal or within an unsealed area in the area covered by the marginal heat seal. The indicia can also be located interiorly of the marginal heat seal for example at a corner or angle formed between adjacent seals with the plastic member being heat sealed to the paper member in the area surrounding the indicia.

6 Claims, 4 Drawing Figures

STERILIZABLE PACKAGE AND METHOD

RELATED APPLICATION

This application is a Continuation In Part of co-pending application Ser. No. 606,510 filed Aug. 21, 1975.

BACKGROUND

This invention relates to an improved sterilizable package wherein color sensitive inks or the like that change color upon sterilization are positioned on the inside of the package and are located so as to prevent the package contents from covering or being contaminated by coming in contact with such inks.

Sterilizable packages or pouches made by marginally heat sealing a clear plastic laminate to surgical grade kraft paper or the like have come into widespread use. The paper portion of such packages is designed to be sufficiently porous to permit gas or steam sterilization but is impervious to bacteria. The plastic laminate is heat sealable to the paper, stable under sterilization conditions, impervious to bacteria and permits visual identification of the package contents. Indicator inks that change color upon sterilization have generally been printed on the exterior, paper side of the package.

Packages such as this are used for medical implements that must be sterile prior to use. The manufacturer or user (such as a hospital or a clinic) is supplied with a package heat sealed around three sides leaving an open end into which the package contents are inserted. The medical implement is then placed in the package and the fourth side is heat sealed to complete the marginal heat seal around the edges of the package. The package and its contents are then subjected to sterilization, either by exposure to ethylene oxide gas or by steam autoclaving. This causes the indicator ink applied to the exterior paper side of the package to change color but this has drawbacks because the indicator ink will change color, being located on the exterior of the package, before the package contents have been exposed to sterilizing gas. This means that sterilization procedures with an extra margin of safety must be followed and the user of the package contents is only assured that the package has undergone sterilization but he has no assurance that the package contents have been exposed to sterilizing gas.

To overcome this it has been proposed to locate the indicator inks closer to the package contents by applying the indicator ink to the inside of the paper member of the sterilizable package (see for example U.S. Pat. No. 3,093,242 to Huyck et al. and U.S. Pat. No. 3,991,881 to Augurt). These efforts, however, have not been entirely satisfactory because the package contents can cover the area imprinted with the indicator ink making it difficult to visually determine the sterile condition of the package and its contents. Moreover, many indicator inks become soft or sticky and some actually run upon exposure to sterilization conditions which means that the package contents can become undesirably contaminated by coming in contact with the indicator inks applied to the interior of the package.

SUMMARY

The present invention provides a sterilizable package and method which overcome these and other drawbacks by segregating the indicator inks from the package interior thereby preventing the package contents from covering or being contaminated by the indicator inks.

The sterilizable package of the invention has a plastic member marginally heat sealed to a paper member to which has been applied indicia, e.g., an indicator ink or inks which change color upon sterilization (gas and/or steam sterilization) to the inside of the package. According to the improvement of the invention the indicia is located in or near the marginal heat seal and is segregated from the package interior to prevent the package contents from covering or being contaminated by coming in contact with the indicia by heat sealing the plastic member to the paper member in the area of the indicia. The indicia can be located within the area covered by the marginal heat seal, within an unsealed area in the area covered by the marginal heat seal, or interiorly of the package adjacent one or more corners or angles formed between adjacent seals. In the last instance, since the indicator inks are within the area enclosed by the marginal heat seal, they are segregated from the package interior by heat sealing the plastic member to the paper member in the area surrounding the inks.

DESCRIPTION OF THE DRAWING

The present invention will be more fully understood from the accompanying drawing taken in conjunction with the following description wherein.

DESCRIPTION

Figure 1:
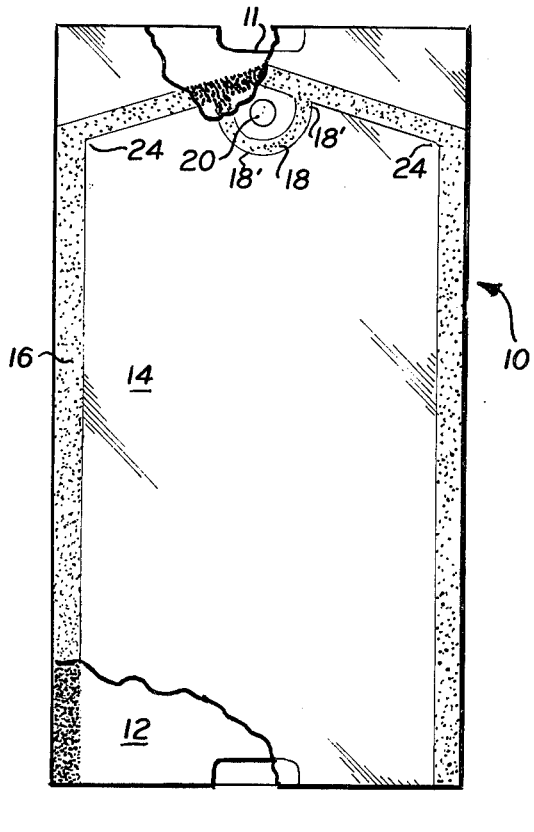
FIG. 1 is a top plan view partly broken away, of a sterilizable package according to the invention taken from the plastic side thereof.

Referring now to FIG. 1 the sterilizable package of the invention is generally identified by reference number 10 and is shown to include a plastic member 14, preferably transparent as shown, marginally heat sealed in the area indicated by reference numeral 16 to a paper number 12. The paper number 12 has applied to the side forming the interior of the package an indicator ink 20 which changes color upon sterilization, that is upon exposure to either gas or steam.

Commonly employed indicator inks are chemically sensitive inks that undergo a distinct visible color change when exposed to sterilization conditions. Certain known indicator inks are sensitive to steam sterilization and other known indicator inks are sensitive to ethylene oxide sterilization.

To prevent the indicator ink 20 from being covered by the package contents 22 (FIG. 2) which in this instance is a surgical sponge for purposes of illustration, and to avoid contamination of the sponge 22 by the indicator ink 20, the area surrounding the indicator ink 20 is heat sealed as shown and identified by reference number 18. If desired one or more gaps or voids can be left in the heat seal 18 as indicated at 18' so as to allow the sterilization atmosphere to come in contact with the indicator ink 20 in the same way that it comes in contact with the item to be sterilized in the package interior.

Figure 2:
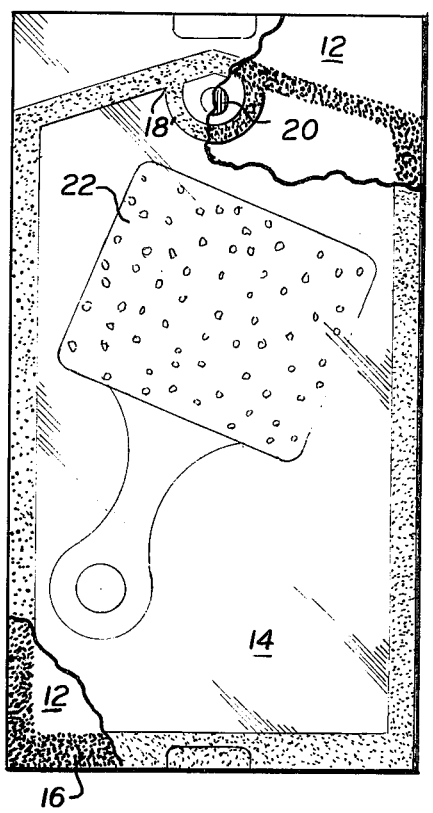
FIG. 2 is a top plan view of the sterilizable package of FIG. 1 illustrating the positioning of a medical implement within the package interior and completion of the marginal heat seal.

FIG. 1 shows a preferred embodiment wherein an inverted V end seal joins two generally parallel side seals which form the marginal heat seal 16 around three sides of the package. The marginal heat seal 16 is completed as shown in FIG. 2 after the item or implement 22 is inserted. In this preferred embodiment the indicator ink 20 is positioned adjacent the apex of the inverter V seal and a crescent-shaped seal 18 between the plastic member 14 and the paper member 12 prevents the package contents from covering or being contaminated by the indicator ink 20.

It is also possible to locate the indicator ink 20 in the area of the angle indicated at 24 formed between the V end seal and the side seals. Positioning the indicator inks in the corners 24 and/or at the apex of the V seal in the center of the end of the package puts the indicator inks as far as possible from the open end of the pouch 10 and makes good use of somewhat wasted space since the V seal is used for opening a sterilized package. Locating indicator inks in the corners 24 as shown in FIG. 1 also makes it possible to use two different indicator inks one for gas sterilization and the other for steam sterilization. Suitable indicia to this effect can be printed within the area where the printing ink per se is occupied, that is within the area enclosed by the crescent seal 18 or a similar shaped seal used in the corners 24, or it can be printed around or adjacent to the area enclosed by the seal 18.

Figure 3:
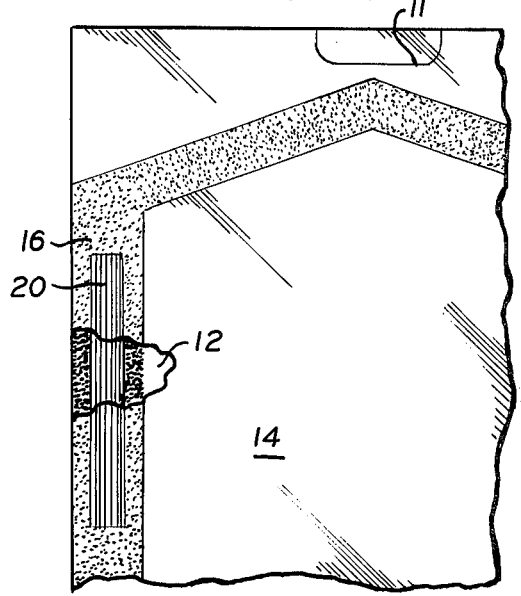
FIGS. 3 and 4 are top plan views partly broken away of sterilizable packages according to the invention showing alternate embodiments as regards the embodiments shown in FIG. 1, both taken from the plastic side of the package.

FIG. 3 shows an alternate embodiment wherein the indicator ink is actually located within the area covered by the marginal heat seal 16. In this instance the indicator ink is printed along a marginal area as shown in FIG. 3 of the paper number 12 and since the plastic member 14 is transparent, the marginal heat seal 16 can be formed right over the indicator ink 20 which remains visible through the transparent plastic member 14. The sterilization medium comes in contact with the indicator ink 20 in the same way that it comes in contact with the package contents to be sterilized namely by passing through the pervious paper number 12. In the embodiments shown in FIG. 1 involving the corners 24 and/or the center portion enclosed by the crescent seal 18, the indicator ink 20 can have indicia printed inside of the area enclosed by the marginal seal 16 or closely adjacent thereto indicating the nature of the indicator ink, that is whether it changes color upon gas or steam sterilization.

In FIG. 3 the indicator ink 20 can be positioned in one or both of the side seals and can be a broken line or a longer solid line as compared to the solid line shown. The indicator ink 20 can also be positioned within the inverted V end seal on one or both sides depending on the intended use for the sterilizable pouch. Where two indicator inks are used, one for steam sterilization and the other for gas sterilization, suitable indicia can appear adjacent the indicator ink 20 itself either in the marginal heat seal area 16 or closely adjacent thereto.

Figure 4:
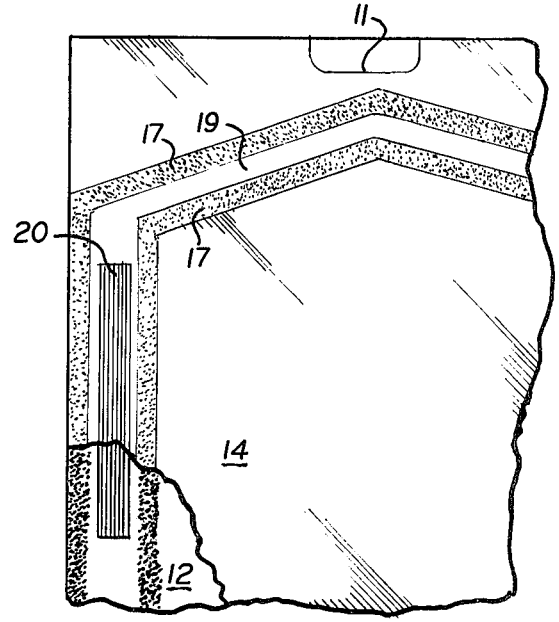

FIG. 4 shows an alternate embodiment wherein two marginal heat seals 17 are formed with a void or unsealed space 19 therebetween. This is commonly known in the industry as a rib seal and in this embodiment the indicator ink 20 is located in the unsealed area 19 which is surrounded by the sealed areas 17. The indicator ink 20 is printed on the paper member 12 in the same manner as in FIG. 3 and if desired voids or free spaces can be left on the innermost rib seal 17 so that the sterilization medium in the package interior can come in contact with the indicator ink 20 in the same fashion it comes in contact with the package contents to be sterilized.

A cutout 11 positioned at one or both ends of the bag is provided to facilitate opening of the package from the V seal end.

In carrying out the method of the invention the paper member 12 is imprinted with the desired indicator ink 20 along with suitable indicia indicating the nature of the indicator ink itself (herein sometimes collectively referred to as indicia that changes color upon exposure to sterilization). The indicator inks are printed on the paper member 12 in the desired position so as to be segregated from the package interior by any of the embodiments shown in FIGS. 1–4. The transparent plastic member 14 is then marginally heat sealed around three sides to the paper member 12 with the indicator ink in the desired location to form the three-sided marginal heat seal 16 as shown in FIG. 1. After the item to be sterilized is inserted into the open end of the package, the marginal heat seal 16 is completed (FIG. 2) and the package is ready for sterilization. The package is then subjected to the desired type of sterilization that is, by steam autoclaving or exposure to ethylene oxide gas, and the sterilization medium permeates the paper member 12 and sterilizes the package contents and at the same time effects a color change in the indicator ink 20. In this fashion, there is a better guarantee that the package contents have been properly sterilized with the indicator inks positioned within the package interior since the color change indicates that the sterilization medium at least penetrated into the interior of the sealed package as shown in FIG. 2. By segregating the indicator ink 20 from the package interior, there is no possibility that the item to be sterilized such as the sponge 22 can cover the indicator ink which would otherwise make it difficult to determine if the package and its contents are in a sterile condition. Moreover, the indicator ink is prevented from contaminating the sterile contents of the package by segregating as described.

Readily available surgical grade kraft paper having the desired porosity characteristics can be employed for the paper member 12. The term "paper" as used herein also applies to synthetic or artificial paper materials made from plastic fibers and the like, as well as conventional paper products having the necessary characteristics used in sterilization packages or pouches. An example of synthetic paper is a spun bonded polyethylene sold by DuPont under the trademark "TYVEK".

The plastic member 14 is generally colorless and transparent and is commonly made from a laminate of a polyester such as polyethylene terephthalate sold under the trademark "MYLAR", and a heat sealable thermoplastic material such as polyethylene, polyprophylene, ethylene vinyl acetate, an ionomer such as DuPont's "SURLYN", co-polymers and mixtures of the foregoing. The polyester layer forms the exterior of the package and the heat sealable thermoplastic material interfaces with the paper number 12 to form the marginal heat seal 16.

Heat sealing the plastic number 14 to the paper number 12 around the margin of the package as shown in FIGS. 1 and 2 of the drawing can be accomplished using conventional heat sealing equipment and techniques. Generally the heat seal 16 is sufficiently wide to guarantee an adequate and complete seal around the margin of the package and in the embodiments shown in FIGS. 3 and 4 the width of the heat seal is chosen to accommodate the indicator ink 20 imprinted in the area to be covered or enclosed by the marginal heat seal 16 or the rib seal 17 (FIG. 4).

What is claimed is:

1. A sterilizable package comprising a plastic member, a paper member, a first heat seal marginally sealing the plastic member to the paper member to define a pouch receptive of an item to be sterilized, indicia borne by the paper member on the inside of the pouch located adjacent to and spaced from said marginal heat seal, said indicia changing color upon sterilization of the package, and at least one second heat seal located interiorly of the marginal heat seal and adjacent to and spaced from the indicia and cooperating with said marginal heat seal to surround and isolate the indicia to prevent the package contents from covering or being contaminated by coming in contact with said indicia.

2. Package of claim 1 wherein the marginal heat seal includes an inverted V seal joining two side seals, said indicia is located adjacent the apex of the V or one or both of the angels formed by the V seal and the side seals and the second heat seal comprises a heat seal in the area surrounding said indicia.

3. Package of claim 2 wherein said indicia is located at the apices of the angles formed between said V seal and said side seals, one of said indicia changing color upon steam sterilization and the other of said indicia changing color upon gas sterilization.

4. Package of claim 1 wherein the marginal heat seal and at least one second heat seal define two unsealed areas surrounded thereby and the indicia located in the first unsealed area changes color upon steam sterilization and the indicia in the second unsealed area changes color upon gas sterilization.

5. Package of claim 1 wherein said paper member is surgical grade kraft paper.

6. Package of claim 1 wherein said plastic member is a laminate of a polyester and a heat sealable thermoplastic material.

* * * * *

UNITED STATES PATENT AND TRADEMARK OFFICE
CERTIFICATE OF CORRECTION

PATENT NO. : 4,091,921
DATED : May 30, 1978
INVENTOR(S) : Robert P. Lewis

It is certified that error appears in the above-identified patent and that said Letters Patent are hereby corrected as shown below:

Title Page - Incorrect drawing appears on Title Page.

Col. 3, l. 45, Insert "heat" before "seal".

Signed and Sealed this

Twenty-eighth Day of November 1978

[SEAL]

Attest:

RUTH C. MASON
Attesting Officer

DONALD W. BANNER
Commissioner of Patents and Trademarks